[19] United States Patent
Kulwicki et al.

[11] Patent Number: 5,131,990
[45] Date of Patent: Jul. 21, 1992

[54] FLUOROPOLYMER HUMIDITY SENSORS

[75] Inventors: Bernard M. Kulwicki, N. Attleboro, Mass.; Robert T. McGovern, Chepachet, R.I.; Thomas C. Conlan, Attleboro, Mass.

[73] Assignee: Texas Instruments Incorporated, Dallas, Tex.

[21] Appl. No.: 684,713

[22] Filed: Apr. 12, 1991

Related U.S. Application Data

[62] Division of Ser. No. 386,335, Jul. 27, 1989.

[51] Int. Cl.$^5$ ............................................... H01C 7/00
[52] U.S. Cl. ........................ 204/153.22; 204/430; 204/422; 428/421; 73/335.02; 338/34; 338/35
[58] Field of Search ............ 204/153.22, 430, 422; 73/335, 336.5; 338/34, 35; 422/98

[56] References Cited

U.S. PATENT DOCUMENTS

| | | | |
|---|---|---|---|
| 3,369,880 | 2/1968 | Mochel | 204/153.22 |
| 3,961,301 | 6/1976 | Fraioli | 73/336.5 |
| 4,083,765 | 4/1978 | Lawson | 204/430 |
| 4,915,816 | 4/1990 | Shakkottai et al. | 73/335 |

Primary Examiner—John Niebling
Assistant Examiner—Bruce Bell
Attorney, Agent, or Firm—John A. Haug; James P. McAndrews; Melvin Sharp

[57] ABSTRACT

A humidity sensor composed of interdigitated electrodes and a material therebetween which is composed of Nafion wherein H+ cites have undergone ion exchange with at least one of NH4+ and Li+, Na+, Ag+ and Mg+.

18 Claims, 1 Drawing Sheet

FLUOROPOLYMER HUMIDITY SENSORS

This application is a division of application Ser. No. 07/386,335, filed July 7, 1989.

CROSS REFERENCE TO PRIOR APPLICATION

This application is an improvement over Ser. No. 07/155,666, filed Feb. 12, 1988, the contents of which are incorporated herein by reference.

BACKGROUND OF THE INVENTION

1. Field of the Invention

This invention relates generally to humidity sensors and, more particularly, to such sensors whose electrical resistance varies in response to changes in humidity in the surrounding atmosphere.

2. Brief Description of the Prior Art

Humidity sensors are generally electrical components which display a parameter change in response to change in humidity of the surrounding atmosphere. A known problem with humidity sensors is long-term drift during exposure to various environmental conditions including certain chemicals.

It is well known that humidity sensors can be fabricated using polyelectrolyte films as humidity dependent A-C resistors. Examples of such prior art are provided in Pat. No. 4,386,336 and Japanese Patent No. 59-44647.

A polyelectrolyte material which is very attractive for humidity sensing because of its excellent thermal and chemical stability is a sulfonated fluoropolymer manufactured by DuPont under the trademark Nafion. Nafion 117 is a polytetrafluoroethylene material with perfluorosulfonic acid groups appended thereto. Efforts to utilize this material for humidity sensing have been made in the past. Lawson (Pat. No. 4,083,765) describes an electrolytic hygrometer that utilizes a hollow fiber formed of Nafion having closely spaced metal electrodes on the inner and outer surfaces. This device is complex, expensive and requires flowing gas of controlled velocity. Laue (NASA Technical Briefs, 1985) used a solid film element with contacts on opposing faces as a humidity dependent capacitor in an RC oscillator circuit. Again, response is likely to be very slow because of the thickness of the film. Lawson et al. (Proceedings of the Sensors Exposition, Detroit, Sep. 15, 1987) described a polymer electrolyte hygrometer that utilized the relatively thick Nafion film embedded in silver epoxy for electrical contacts. Response time was faster because the sensing mechanism involved detecting changes in surface conduction due to adsorption of water on the outer surface of the strip. The device appeared to work well in a harsh environment, in particular, a paper mill, however it required complex and expensive electronics. Due to reliance upon surface conduction, the device may be susceptible to contamination, although this did not appear to be a serious problem in the paper mill.

Huang describes in Pat. No. 4,681,855 humidity sensors that utilize fluoropolymers similar to Nafion but with weak (e.g. carboxylic) as well as strong (sulfonic) acid groups appended to the fluoropolymer backbone. The advantage of using combined weak/strong acids was to have the ability to tailor the response characteristics for different applications (e.g., dry or moist atmosphere). Huang also contended that the purely sulfonated fluoropolymer did not possess sufficient sensitivity above 40% relative humidity and that adding the —COOH moiety improved the response at high humidity.

BACKGROUND AND SUMMARY OF THE INVENTION

In view of the potential for excellent thermal and chemical stability of Nafion, these properties being highly desirable in humidity sensors, where, as noted above, a major problem is long-term drift, an investigation was conducted by applicants herein of Nafion film A-C resistors as bulk-effect devices on interdigitated comb electrodes. Nafion 117 is a member of the perfluorsulfonic acid polymer family that has an equivalent weight of 1100, i.e., 1100 grams of resin contain 1 gmol polyelectrolyte (sulfonic acid) moieties. A lacquer which was a 5% solution of Nafion-117 in water and lower aliphatic alcohols was used to prepare bulk-conducting polyelectrolyte thin films on interdigitated comb electrodes of the type known in the prior art as set forth, for example, in Pat. No. 3,891,958. The resistor pattern was formed on an alumina base. The humidity sensitivity was excellent even above 40% relative humidity and hysteresis was low. However, subsequent effort to reproduce the original response resulted in coatings which exhibited usually greater and highly variable hysteresis which did not appear to correlate directly with film thickness. Further experimental efforts demonstrated that hysteresis can be greatly reduced by cycling the film several times between high and low humidity.

In view of an article in Journal of the Electrochemical Society, 135(6), pp. 1603–4, 1988, wherein it was shown that plasma-associated cross-linking could reduce the permeability of Nafion films, plasma post treatment of Nafion humidity sensors was investigated as a means for improving stability. The drift was reduced by about 50 percent. However, again, constant reproducible electrical response could not be obtained.

Accordingly, in accordance with the present invention, the acid H+ of the sulfonic acid in Nafion, a perfluorosulfonic acid substituted polytetrafluoroethylene as described in the above noted Lawson patent and which description is incorporated herein by reference, is replaced by $NH_4+$ and/or $Li+$ ions to provide a material which provides a predictable change in electrical parameter with change in humidity and without appreciable drift. Also, drift is reduced by cycling the completed humidity sensor from low relative humidity in the range of 20 to 30% and preferably 20% to high relative humidity in the range of 80 to 90% and preferably 90%, preferably at least twice, first at about 23 degrees C. and repeated at 4 degrees C. The choice of the temperatures is arbitrary and is based upon the fact that 23 degrees C. is approximately normal room temperature and 49 degrees C. is approximately the highest temperature to which the sensor is likely to be exposed.

Briefly, Nafion essentially consists of a perfluorosulfonic acid substituted polytetrafluoroethylene as described in the above noted Lawson patent, which description is incorporated herein by reference, and generically is a polytetrafluoroethylene backbone with ionogenic groupings appended thereto, these groupings containing sulfonic acid in the case of Nafion, the H+ of the sulfonic acid being replaceable by other ions.

In the case of Nafion, the resistivity and stability of sensors with and without the ion exchange were tested and it was determined that both properties are improved under certain conditions as follows:

resistivity is reduced in the sequence: K>H>NH4->Na>Li stability is best in the sequence (anion): Cl>OH stability is best in the sequence (cation) NH4>Na>H>Li Low resistivity and high stability are desired. Best results have been obtained by ion exchange from the chloride solutions. Pure NH4Cl exchanged sensors have too high resistivity. A mixture of NH4Cl, LiCl and/or NaCl would appear to yield acceptable results. It also appears that the anion is very important.

The ion exchange is perfomed using a 0.1 to 0.5 molar and preferably a 0.2 molar solution by immersion at room temperature for 15 to 60 minutes and preferably 30 minutes. Suitable salts include chloride, acetate, citrate and hydroxide. The main requirement is solubility in water. The specific anion has no effect on resistivity, but stability testing in dilute alcohol vapors suggests that sensors exchanged from chloride bath are more stable than those exchanged from hydroxide.

The replacement can take place by dipping a film containing the Nafion into an aqueous solution of the ion for a specified time, e.g., 15 to 60 minutes, preferably 30 minutes. NH4+ and Li+ exchange are preferred and provide desirable results. Suitable salts include NH4Cl, NH4OH, LiCl, LiOH, however good results have also been obtained using acetates and citrates. The main requirement is for the salt to be soluble in water. Concentrations from 0.1 to 0.5 M, preferably 0.2 M, are suitable.

The NH4+ and Li+ exchanged films exhibited excellent stability on exposure to dilute alcohol vapor (vapor above a solution of 5% ethanol +5% methanol in water). The stability of these films under this exposure was comparable to that of the best commercially available resistive sensors.

Though experimental results to date have only been obtained using ions of NH4, Li, Na, K, Ag, Mg and combinations of NH4:Li of 1:1, 3:1 and 9:1, it is apparent that other ions could also provide beneficial results. Nominal resistances for 5 micron thick films on combs with geometry of 4×4 mm and 10 fingers, 0.2 mm finger width and 0.1 mm gaps are:

|  | nominal resistance, kohms at 1 kHz, 24° C., 33% RH |
|---|---|
| H+ form (as cast - no exchange) | 5,000 |
| NH4+ exchanged | 2,000 |
| Na+ exchanged | 1,000 |
| 9:1 NH4+:Li+ exchanged | 750 |
| 3:1 NH4+:Li+ exchanged | 500 |
| Li+ exchanged | 250 |

Practical sensors should have resistances below about 1,000 kohms at 33% RH. Thicknesses above 5 microns may not be feasible because of increased response time, hysteresis and cost. Thinner films have higher resistance and poorer repeatability of sensor response among members of a manufacturing lot. The best design trade-off among all of the requirements appears to be thickness in the range 3 to 5 microns, cation exchange NH4-Li (or Na, Li, Na-Li) and anion Cl. Response times of about 5 to about 10 seconds are obtained at 24 degrees C. at thicknesses of from about 3 to about 5 microns.

A test of the Nafion films before and after ion exchange in the manner noted above indicated that the resistance thereof was reduced to about one half when the H+ was replaced by NH4+ and was reduced to about one twentieth when the H+ was replaced by Li+. Furthermore, resistances between those provided by Li+ exchange and NH4+ exchange were provided by utilizing both exchanges simultaneously in different proportions. Low resistances are highly desirable.

DESCRIPTION OF THE PREFERRED EMBODIMENT

EXAMPLE 1

Figure 1:
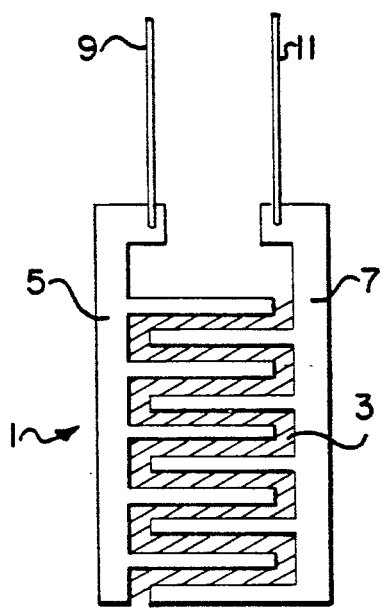
FIG. 1 is a schematic diagram of a humidity sensor formed in accordance with the present invention.

A humidity sensor 1 was formed by doctor-blade casting a film of Nafion-117 3 (from a 5% solution in water and lower aliphatic alcohols) on an alumina substrate between electrodes of an interdigitated electrode pattern formed by gold electrodes 5 and 7 as shown in FIG. 1. Also shown are terminals 9 and 11 which couple the electrodes 5 and 7 to an external device. The electrode pattern was approximately 4 mm on a side with ten gold fingers 0.2 mm wide and spaced 0.1 mm apart. The sensor was formed in standard manner. The Nafion film had a thickness of 2 micrometers.

Figure 2:
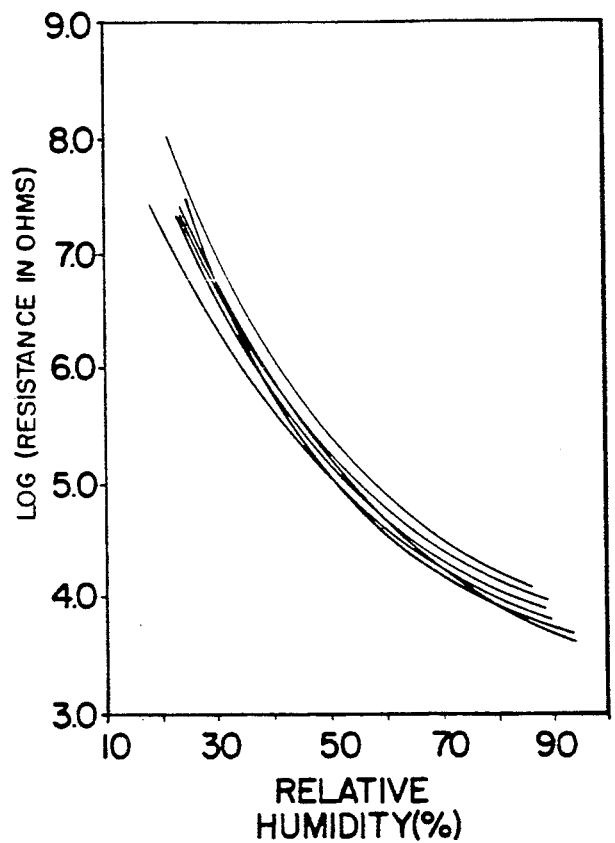
FIG. 2 is a graph of the log of resistance in ohms v. relative humidity in percent for the humidity sensor in accordance with the present invention after ammonium ion exchange.

The humidity sensor 1 of FIG. 1 was then dipped into a 0.5 molar solution of ammonium chloride for 15 minutes. The film was then rinsed in deionized water, air dried, cured at 135 degrees C. for 1 hour and conditioned by cycling the relative humidity between 30 and 90 percent at 24 and 49 degrees C. The sensor was then tested under exposure to dilute alcohol vapor (vapor above a solution of 5% ethanol +5% methanol in water) for 101 days. The stability under this exposure was comparable to that of the best commercially available sensors. The results of exposure of the NH4+ exchanged sensor to dilute alcohol vapor is displayed in FIG. 2. Even after more than 3 months, the response characteristic remained within a narrow band.

The resistance in kilohms at 1 kHz, 24 degrees C. and 33% relative humidity was measured across the humidity sensor of Example 1 prior to ion exchange with NH4+ and found to be 10,000 kohms. After ion exchange with the NH4+ the resistance was 5,000 kohms.

EXAMPLE 2

Example 1 was repeated except that the humidity sensor was dipped into a 0.5 molar solution of lithium hydroxide for 15 minutes. The film was then processed as in Example 1. The sensor was then tested under exposure to dilute alcohol vapor as in Example 1. The stability was comparable but slightly inferior to that of Example 1. The resistance in kilohms at 1 kHz, 24 degrees C. and 33% relative humidity was measured across the humidity sensor of Example 2 prior to ion exchange with Li+ and found to be 10,000 kohms. After ion exchange with the Li+ the resistance was 500 kohms.

EXAMPLE 3

Example 1 was repeated except that the humidity sensor was dipped into a solution of 0.1 molar ammonium hydroxide and 0.1 molar lithium hydroxide for 30 minutes. The film was then processed as in Example 1. The sensor was then tested under exposure to dilute alcohol vapor as in Example 1. The stability was comparable but slightly inferior to that of Example 1. The resistance in kilohms at 1 kHz, 24 degrees C. and 33% relative humidity was measured across this humidity sensor prior to ion exchange with NH4+ and Li+ and found to be 10,000 kohms. After ion exchange with the NH4+ and Li+ the resistance was 900 kohms.

Results similar to those described above were obtained using the chloride, acetate and citrate solutions with different moralities and soaking times. No significant difference in average resistance or variability thereof was observed.

It is apparent from the above examples that the resistance of the ion exchanged Nafion film can be adjusted as desired (i.e. for the dimensions and conditions used in the example, from 500 to 10,000 kohms) by varying the ratio of NH4+ to Li+ in the ion exchange procedure.

The decrease in resistance due to Li+ is very desirable in a device since special precautions to guard the circuitry are not needed to obtain consistent output at low humidity.

Figure 3:
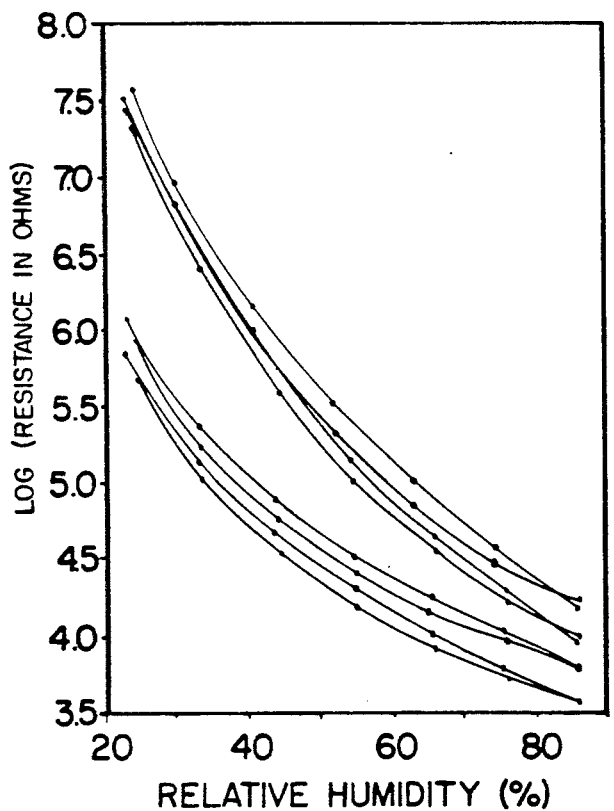
FIG. 3 is a graph showing the log of resistance in ohms v. relative humidity in percent for several different humidity sensors wherein the Nafion has undergone ion exchange with different ions.

FIG. 3 is a graph of humidity response of a selected sensor from each group. In order to obtain an optimum combination of low resistance and stability, it is desirable to utilize combined ammonium ion and lithium ion exchange.

Though the invention has been described with respect to specific preferred embodiments thereof, many variations and modifications will immediately become apparent to those skilled in the art. It is therefore the intention that the appended claims be interpreted as broadly as possible in view of the prior art to include all such variations and modifications.

What is claimed is:

1. A method of fabricating a humidity sensor comprising the steps of:
   (a) providing a humidity sensor having a humidity responsive element consisting of the reaction product of polytetrafluoroethylene with ionogenic grouping appended thereto and an aqueous solution of a compound taken from eh class consisting of lithium compounds, ammonium compounds, sodium compounds, potassium compounds, silver compounds, magnesium compounds and combinations thereof; and
   (b) cycling said sensor between a low relative humidity in the range of the from about 20 to about 30 percent to a high relative humidity in the range of about 80 to 90 percent.

2. The method of claim 1 wherein said lithium compounds are taken from the class consisting of lithium chloride, lithium hydroxide, lithium acetate and lithium citrate.

3. The method of claim 1 wherein said ammonium compounds are taken from the class consisting of ammonium chloride, ammonium hydroxide, ammonium acetate and ammonium citrate.

4. The method of claim 2 wherein said ammonium compounds are taken from the class consisting of ammonium chloride, ammonium hydroxide, ammonium acetate and ammonium citrate.

5. The method of claim 1 wherein said cycling is performed at least two times.

6. The method of claim 2 wherein said cycling is performed at least two times.

7. The method of claim 3 wherein said cycling is performed at least two times.

8. The method of claim 4 wherein said cycling is performed at least two times.

9. A method of fabricating a humidity sensor comprising the steps of:
   (a) providing a humidity sensor having a humidity responsive element consisting of the reaction product of polytetrafluoroethylene with ionogenic grouping appended thereto and an aqueous solution of each of an ammonium compounds taken from the class consisting of ammonium chloride, ammonium hydroxide, ammonium acetate and ammonium citrate and a lithium compound taken from the class consisting of lithium chloride, lithium hydroxide, lithium acetate and lithium citrate.

10. The method of claim 1, further including the step of maintaining the ambient temperature during said cycling in the range of about 24 degrees C.

11. The method of claim 2, further including the step of maintaining the ambient temperature during said cycling in the range of about 24 degrees C.

12. The method of claim 3, further including the step of maintaining the ambient temperature during said cycling in the range of about 24 degrees C.

13. The method of claim 4, further including the step of maintaining the ambient temperature during said cycling in the range of about 24 degrees C.

14. The method of claim 5, further including the step of maintaining the ambient temperature during said cycling in the range of about 24 degrees C.

15. The method of claim 6, further including the step of maintaining the ambient temperature during said cycling in the range of about 24 degrees C.

16. The method of claim 7, further including the step of maintaining the ambient temperature during said cycling in the range of about 24 degrees C.

17. The method of claim 8, further including the step of maintaining the ambient temperature during said cycling in the range of about 24 degrees C.

18. The method of claim 9, further including the step of maintaining the ambient temperature during said cycling in the range of about 24 degrees C.

* * * * *